United States Patent [19]

Surer

[11] Patent Number: 5,013,313

[45] Date of Patent: May 7, 1991

[54] DEVICE FOR FIXATION OF PART ON A SUPPORT, ESPECIALLY OF AN IMPLANT ON A BONE

[76] Inventor: Patrick Surer, Rue du Prieuré de Béré, 44110-Chateaubriant, France

[21] Appl. No.: 357,766

[22] Filed: May 26, 1989

[30] Foreign Application Priority Data

May 30, 1988 [FR] France ................. 88 07170

[51] Int. Cl.⁵ .............................................. A61F 5/04
[52] U.S. Cl. ........................................ 606/60; 606/72; 606/73
[58] Field of Search ............... 128/92 R, 92 Z, 92 ZZ, 128/92 ZW, 92 YV, 92 YP, 92 YL, 92 YF, 92 YE; 411/107, 109, 368, 369, 396, 533; 606/60-75

[56] References Cited

U.S. PATENT DOCUMENTS

| | | |
|---|---|---|
| 2,376,089 | 5/1945 | Savangeau . |
| 2,550,867 | 5/1951 | Rosan . |
| 4,059,102 | 11/1977 | Devas ........................... 128/92 YF |
| 4,388,921 | 6/1983 | Sutter et al. ............... 128/92 YP X |
| 4,628,923 | 12/1986 | Medoff ................................. 606/65 |
| 4,683,108 | 7/1987 | Balog ................................. 376/260 |
| 4,711,760 | 12/1987 | Blaushild ....................... 411/109 X |
| 4,793,335 | 12/1988 | Frey et al. ........................ 128/92 R |

FOREIGN PATENT DOCUMENTS 2254298 12/1973 France .
2519545 1/1982 France .

Primary Examiner—Robert A. Hafer
Assistant Examiner—Kerry Owens
Attorney, Agent, or Firm—Mason, Fenwick & Lawrence

[57] ABSTRACT

This invention relates, in particular, to a device for attachment of a part (10) on a support (12) with the aid of at least one fixation member such as a screw (14) comprising a head (18) and a rod (16) anchored in the substance constituting the support, the part (10) comprising a passage (34) through which passes the rod (16) and a support surface for the head (18). The device is completed by a supplementary locking member (46) threaded externally and cooperating with a complementary threading provided in the part (10) in order to lock the head of the fixation member relative to the said part and to apply it against the support surface.

Application in particular for the fixation of implants or ancillary material on bones.

19 Claims, 3 Drawing Sheets

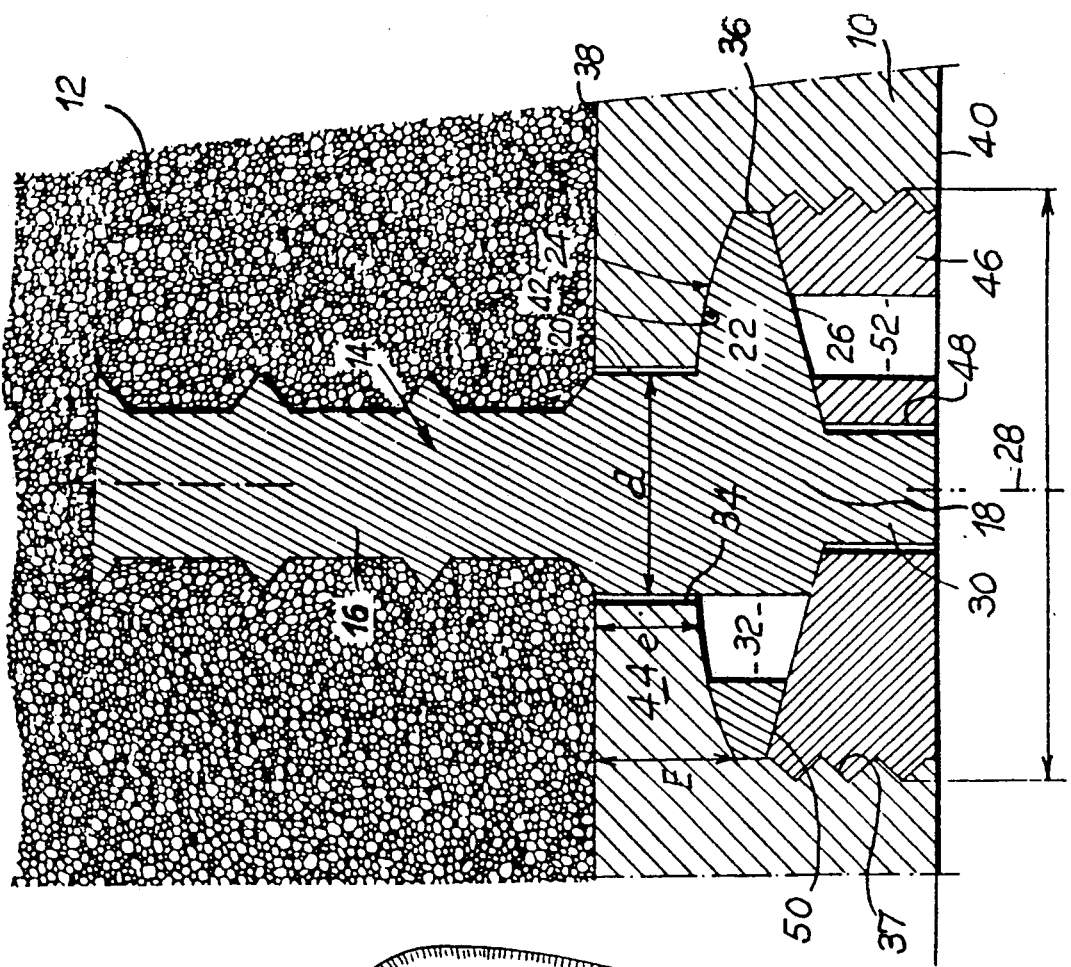
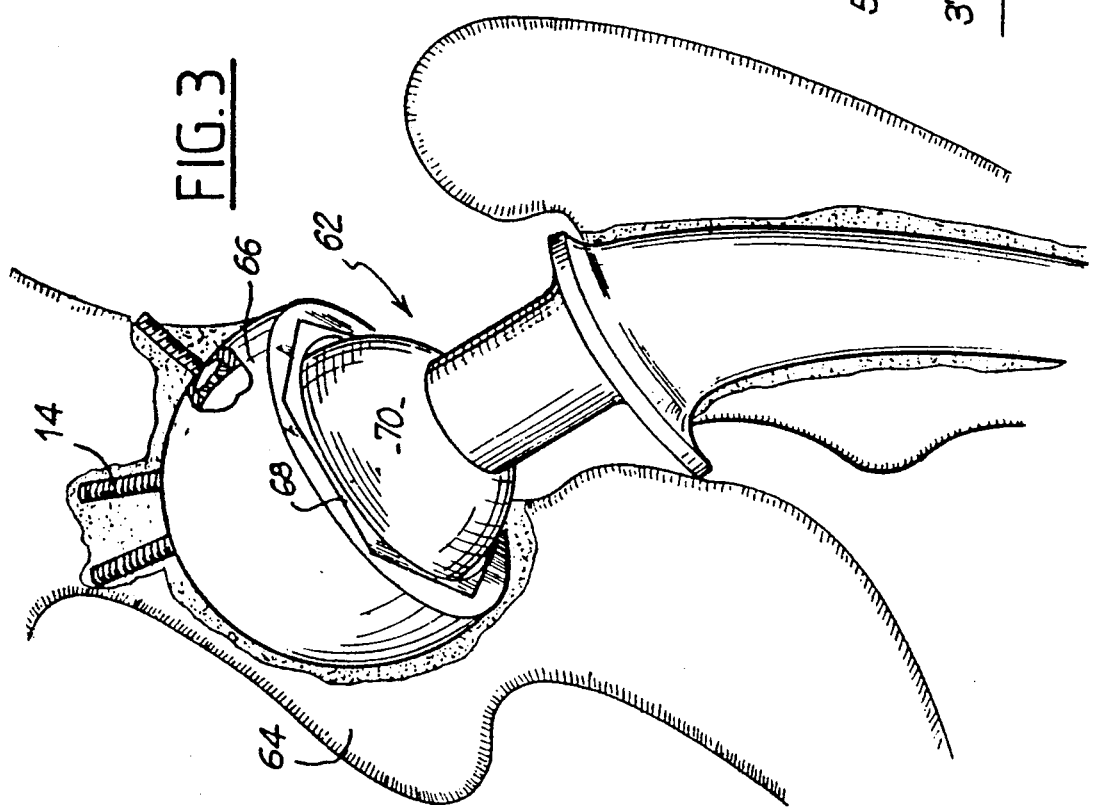

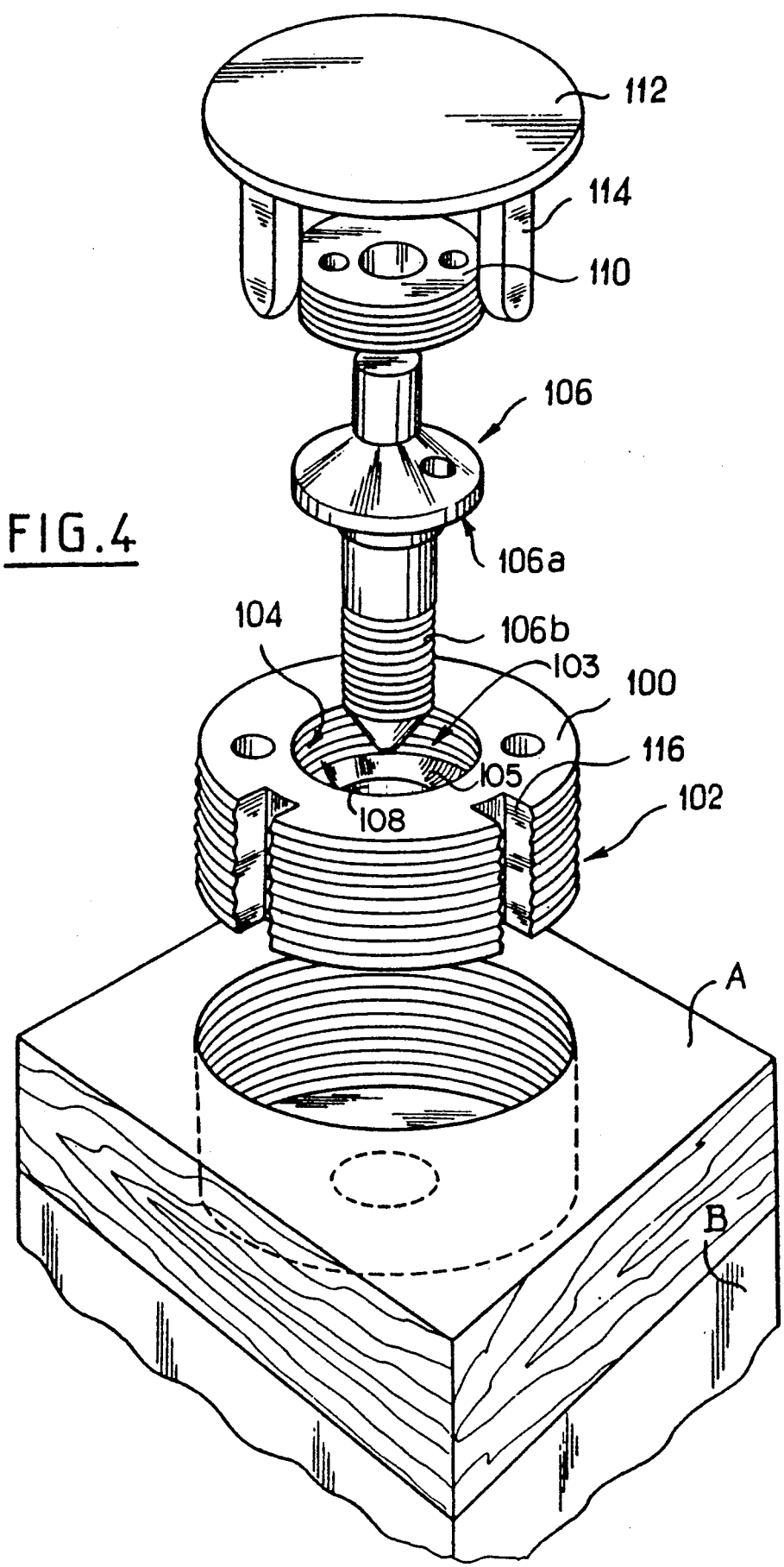

DEVICE FOR FIXATION OF PART ON A SUPPORT, ESPECIALLY OF AN IMPLANT ON A BONE

The present invention relates to a device for attachment of a part on a support with the aid of at least one fixation member anchored in the support.

It is known to fix a part on a support with the aid of screws comprising a head and a threaded rod, the latter passing through the part and being screwed into the substance constituting the support, while the head comes into contact with the part.

The screwing of the screw into the support results in a compression stress at the contact between the part and the support, which is intended to generate frictional forces at the part-support interface which are to prevent any relative movement of the part relative to the support.

A first problem arises, in the case where the substance of the support is altered at the interface with the part, because the frictional forces decrease until they become non-existent, and this renders the part sensitive to stresses in directions perpendicular to its longitudinal axis and can bring about the appearance of a play of the screw in the support and then, in the long run, its extraction, and at the very least gives the part a certain freedom which is not tolerable in certain applications.

This is the case with a concrete wall, covered by a finishing layer of low hardness, on which a part is to be fixed with the aid of at least one screw. The finishing layer may become altered and, although the screw is fixed in the concrete and is perfectly anchored, the part acquires a certain freedom of movement relative to the wall, this being prejudicial to the good quality of the assembly. Under the effect of repeated loading-unloading cycles, which lead to relative movements of the part relative to the screw, the latter may acquire a certain mobility by reason of progressive deterioration, about its threads, of the substance of the support, in this case concrete.

For certain uses the problem proves even more considerable, especially in the case of surgery where implants have to be fixed on bones. For example, in the case of a fracture it is necessary, in order to achieve a stable assembly, to suppress any relative movement of the fragments as well as any movement of these fragments relative to the implant.

Moreover, impaction phenomena may occur between the bone fragments or between these fragments and the implant, this leading to a movement of the implant relative to the screw, if it is considered that there is no movement of the screw relative to the bone in which it is screwed. The assembly is then unstable and the initial geometry is not retained.

An improvement of an assembly of a part on a support with the aid of screws consists in orienting the longitudinal axes of the screws in an oblique fashion with respect to each other.

In this case, the deterioration of the interface confers a certain freedom on the part which, when it is subjected to stresses, tends to exert couples on the screws, since the head of the screw is free in translation and in rotation relative to the part. The screw axis previously divergent relative to the direction of the extraction force gradually comes to be parallel to the latter, facilitating the extraction.

Also known (U.S. Pat. No. A-683,108) is a device used in a nuclear reactor and permitting the locking and replacement of screws. This device comprises an expansion-locking cup which is received in a seat in the part in which is also arranged the head of the screw, and which is integral in rotation with this head. In this way the screw head is prevented from turning by the cup, and it is also retained in the event of an accidental breaking of the rod. However, such a device has disadvantages, such as not solving the problem mentioned hereinabove. In effect:

it does not provide a significant axial resistance to the axial stresses tending to remove the head of the screw from its adjacent support surface, since this resistance is limited to the force required to deform the lateral wall of the cup;

in the same way, it does not achieve an effective attachment of the screw head and the part against which it bears, because the cup does not exert any axial stress on the head of the screw;

it necessitates quite specific equipment for effecting the expansion of the lateral wall of the locking cup;

it is not demountable, since the deformation of the cup is permanent.

The object of the present invention is to provide a device for attachment of a part and a support with the aid of at least one fixation member, which remains stable when the support substance is susceptible of deteriorating at the part-support interface, and which affords improved resistance to extraction. This device should, furthermore, be simple, inexpensive, and easy to put into position and to remove.

To this end, it relates to a device for attachment of a part on a support with the aid of at least one fixation member comprising a head and a rod anchored in the support substance, the part delimiting a passage through which passes the rod of the fixation member and a countersink whose diameter is greater than that of the head of the fixation member in such a way as to define a base constituting a support surface for the said head, a supplementary locking member being received and fixed in this countersink, characterized in that the supplementary locking member is threaded externally and cooperates with an internal thread made in the lateral wall of the countersink, this locking member exerting on the head of the fixation member an axial compression stress which applies it against the base of the countersink.

The invention also relates to an assembly formed by means of at least one such device, as well as to its use in the surgical domain.

The invention will be described hereinbelow with reference to the attached drawings in which:

FIG. 1 shows a cutaway view of a device according to the invention;

FIG. 3 is a perspective view with extraction of a device according to the invention used for the fixation of a cotyloid part improved for this purpose;

FIG. 4 is an exploded view of an embodiment variant.

Figure 2:
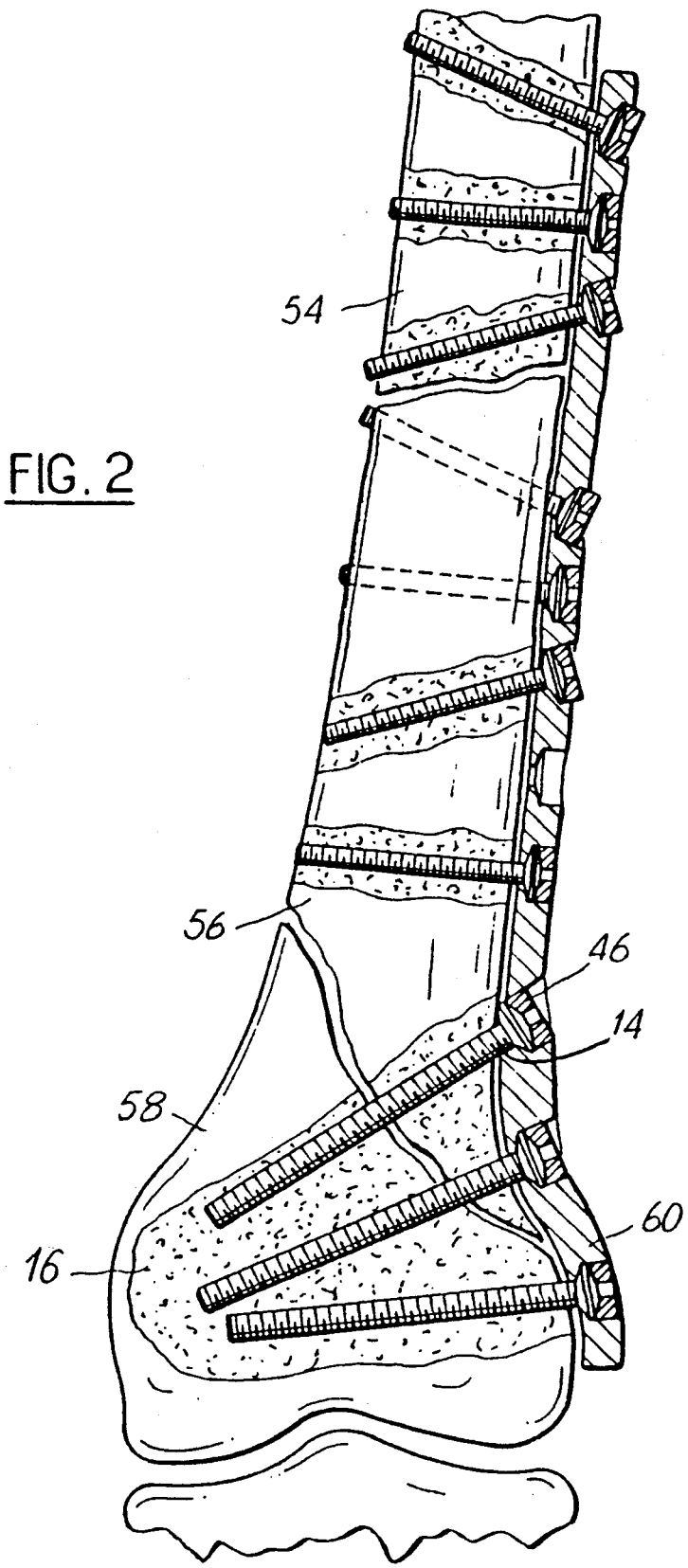
FIG. 2 shows a device with a plate and screws according to the invention.

FIG. 1 shows a device according to the invention providing for the fixation of a part 10 on a support 12 with the aid of a screw 14.

This screw comprises a threaded rod 16 which penetrates into the substance constituting the support and a head 18 which cooperates with the part 10. The head 18 comprises a non-threaded cylindrical intermediate section 20 of diameter "d", a flange 22 of a diameter "D", greater than the diameter d, whose face 24 oriented towards the rod is convex and whose opposite face 26 is preferably truncated, and also a cylindrical pin 30.

Moreover, in the flange, bores 32 are provided, distributed evenly. In the example shown, there are three bores arranged at 120°.

The part 10 comprises a passage 34 and a countersink 36 leading respectively to the faces 38, directed towards the support, and 40, directed towards the outside.

The passage 34 is of a slightly greater diameter than the diameter d. As regards the countersink 36, it is coaxial with this passage. It additionally comprises an internal thread 37 which preferably has a pitch which is the opposite of that of the screw. The base 42 of the countersink is concave in order to cooperate, by means of complementarity of shape, with the face 24 of the flange.

The thickness of the zone 44 which surrounds the passage 34, between the face 38 and the base 42 of the countersink, increases progressively radially towards the outside from e to E.

A threaded locking member 46, which will also be designated by the term screw, cooperates with the threaded section of the countersink 36. This screw 46 comprises a bore 48 centered so as to be coaxial with the screw and adapted so as to receive the pin 30 with a slight play.

The end face 50 of the screw 46 has a profile complementary to that of the face 26 of the flange 22.

The locking screw 46 is also provided with bores 52 analogous to the bores 32 of the flange and distributed in the same fashion.

The sizes of the various elements which have just been described are mutually related.

Thus, when the flange 22 comes into contact with the base 42 of the countersink 36, the pin 30 must be flush with the accessible face 40 without protruding. Similarly, the length of the locking screw 46 must be such that, when its end 50 comes to bear on the face 26 of the flange, this screw is flush with the accessible face 40 without protruding.

Such a device is put into position in the following manner: the screw 14 is screwed into the support 12 to the desired depth, for example until the part 10 comes into contact with the support, but nevertheless without exerting a noticeable pressure on this support. This operation is carried out using a tool (not shown) comprising lugs cooperating with the bores 32.

The locking screw 46 is screwed into the countersink 36, preferably using the same tool as before, to such an extent as to apply the flange 22 firmly against the base 24 of the countersink, consequently ensuring the fixation of the screw 14 relative to the part 10.

By virtue of this efficient fixation, the axial stresses exerted on the part are transmitted to the support substance by way of the threads of the screw 14, without intervention of the interface between the part and the support. In contrast to the known arrangements, the fixation of the part 10 and the support 12 does not depend on a compression stress applying them one against the other nor, consequently, on the frictional forces at their interface, but results from a sealing effect achieved by the anchoring of the fixation member (screw 14 or other) in the support, then the fixation of the part 10 on this member by means of the screw 46.

The transverse forces are taken up by the intermediate section 20 and the pin 30 which, respectively, bearing on the walls of the passage 34 and on the walls of the bore 48 of the locking screw 46 oppose the rotation of the screw relative to the plate, generated by such components.

In one variant the fixation screw is screwed into the support without the part coming directly into contact with the latter. This may correspond to the case where a layer of a material of low hardness (not shown) is interposed between the support 12 and the part 10.

According to another variant the screw 14 can be replaced by a nail or other fixation member which is nonthreaded and simply comprises a rod anchored in the substance of the support 12.

FIG. 2 shows an application of the invention in the medical field, where the support 12 in FIG. 1 consists of a femur 54 having suffered a double fracture of the epiphysis and the diaphysis. The part 10 is in this case a plate 60 which holds the two fragments 56 and 58 in position.

This plate comprises several fixation screws of the type described hereinabove, of which the rod passes through the plate and of which the head is fixed in the plate by corresponding locking screws.

In this application the substance of the support comprises the bone formed by the cortical osseous substance itself and the spongy bone of low mechanical resistance arranged in the central portion of the bone.

The seats of the fixation screws, that is to say the passages and the countersinks, are oriented in such a way that the axes of the screws are oriented obliquely with respect to each other, this increasing the resistance to extraction.

Similarly, in order to improve the stability of the fixation screws, these generally pass right through in order to cooperate with that portion of the bone which is most mechanically resistant, that is to say the osseous substance situated opposite the plate.

In this FIG. 2 the fragment 58 is held in position relative to the plate even in the case of a deterioration of the osseous substance at the interface with the plate. Indeed, the screws are immobilized relative to the fragment 58 and, as the screws are themselves immobilized relative to the plate, the fragment 58 retains its initial position both in translation and in rotation about one of the screw heads.

FIG. 3 shows another application of the invention in the medical field, namely the fixation of a cotyloid part 62 on the iliac bone 64 in the case of a hip prosthesis. The shell 66 of the cotyloid part 62 is substantially hemispherical and comprises holes distributed over its surface and intended to receive fixation screws 14 and locking screws 46 such as described hereinabove.

The internal shape of the shell of the cotyloid part is adapted so as to receive a jacket 68 covering the holes and the screw heads, which is intended to cooperate with a ball 70 of a section complementary to the cotyloid part.

This jacket 68 must be immobilized in rotation relative to the shell and, for this purpose, they both have, respectively externally and internally, the shape of a truncated pyramid.

In this case, when the cotyloid part is subjected to compression stresses, these are taken up by the locking screws which suppress any movement of the cotyloid part relative to the fixation screws and, therefore, any movement of the cotyloid part relative to the bone, since the fixation screws are anchored in the osseous substance.

It is possible, if this proves necessary, to interpose material in order to fill the cavities which result from the fact that the cotyle in which the cotyloid part is lodged can become deteriorated. This material is not subjected to compression stresses or shearing forces since these are taken up by the screws directly in the osseous substance of the iliac bone.

The anchorages which the screws constitute can thus be at a relatively considerable distance from the part.

In the medical field the device according to the invention is not limited to single plates and cotyloid parts but is applied to the fixation of all types of implants or ancillary material, that is to say material fixed in a temporary manner and permitting a prosthesis to be positioned.

In the example in FIG. 4 the invention is adapted to the case of a non-metallic part 10 the material of which does not lend itself very well to the formation of a tapped countersink of relatively small diameter. In order to resolve this difficulty, a metallic gusset 100 is provided which comprises an external thread 102 and a countersink 103 provided with an internal thread 104. This gusset delimits a support surface 105 for the head 106a of a fixation member 106 and a passage 108 for the rod 106b of this fixation member. The device is completed by an externally threaded locking member 110 and also by a cap 112 provided with tabs 114 which engage in grooves 116 made in the periphery of the part 100.

The use of such a device is as follows: a drill is used to pierce a drill hole into the two elements A, B to be assembled, then a shell drill is used to form, in the element A, a seat intended to receive the part 100. The latter is screwed into this seat, then the fixation member is fixed in the element B, the locking member is screwed into the part 100 and, finally, the cap 112 is put into position so as to ensure the locking of the gusset relative to the element A.

Although the use of the invention is of particular interest in the surgical field, it can also afford great advantages in other sectors, such as construction and do-it-yourself and can replace the holdfasts or wall anchors which necessitate the use of plaster, cement or other sealing material and do not offer the same possibilities, in particular of disassembly.

I claim:

1. An assembly for securing two elements of different hardness, including:
   (a) a support made of a first material of a first hardness;
   (b) a part made of second material of a second hardness being harder than said first hardness, said part including:
      (1) a cylindrical passage in said part and
      (2) a countersink having internal threads and a first diameter, axially aligned in said part with said passage, including a base; and
   (c) fastener means for affixing said part and said support and for transferring compressive stress laterally into said part without causing substantial compression at the interface between the support and the part, said fastener means being anchored in said support and in said part, and said fastener means comprising:
      (1) a head having a second diameter less than said first diameter,
      (2) a rod secured to said support, said rod being axially aligned with and secured to said head, and
      (3) an externally threaded locking member being threadedly received by said countersink internal threads.

2. An assembly for securing two elements of different hardness, including:
   (a) a support made of a first material of a first hardness;
   (b) a part made of second material of a second hardness being harder than said first hardness, said part including:
      (1) a cylindrical passage in said part and
      (2) a countersink having internal threads and a first diameter, axially aligned in said part with said passage, including a base; and
   (c) fastener means for affixing said part and said support and for transferring compressive stress laterally into said part without causing substantial compression at the interface between the support and the part, said fastener means being anchored in said support and in said part, and said fastener means comprising:
      (1) a head having a second diameter less than said first diameter,
      (2) a threaded rod threadedly secured to said support, said rod being axially aligned with and secured to said head, and
      (3) an externally threaded locking member being threadedly received by said countersink internal threads;
   and wherein said countersink internal threads are tapped with a pitch opposite that of said threaded rod,
   and wherein said head of said fastener and said locking member further include complementary means for laterally securing said fastener and said member,
   and wherein said complementary means comprise a cylindrical pin axially aligned with and secured to said head and a cylindrical bore in said locking member,
   and wherein said head of said fastener includes plural recesses for cooperating with an assembly tool.

3. An assembly for securing two elements of different hardnesses including:
   a support made of a first material of a first hardness,
   a part made of a second material of a second hardness, said second hardness being harder than said first hardness;
   an externally threaded gusset threadedly secured in said part, said gusset including:
      a first frustoconical passage partially extending through said gusset,
      a second cylindrical passage extending through said gusset in axial alignment with said first passage;
      a countersink having internal threads and having a first diameter measurement, axially aligned in said part with said passage, including a base;
   fastener means for affixing said part and said support without causing compression stress between said part and said support, said fastener mean being anchored in said support and in said part, and said fastener means comprising:
      a head having a second diameter less than said first diameter and a frustoconical shape for seating engagement with said first passage in said gusset, and a threaded rod threadedly secured to said support, said rod being axially aligned with and secured to said head; and an externally threaded locking member being threadedly received by said countersink internal threads, wherein said gusset further includes a peripheral surface having plural longitudinal grooves, and wherein said assembly further includes a cap having plural longitudinal tabs adapted to fit tightly in said grooves.

4. The assembly of claim 3, wherein said assembly includes second fastener means for affixing said part and said support and for transferring compression stress of said part and said support laterally into said part, said second fastener means being anchored in said support and in said part at an angle oblique to said first fastener means, and said second fastener means comprising:

a head having a second diameter less than said first diameter and a frustoconical shape for seating engagement with said first passage in said gusset, and a threaded rod threadedly secured to said support, said rod being axially aligned with and secured to said head.

wherein said gusset further includes a peripheral surface having plural longitudinal grooves, and wherein said assembly further includes a cap having plural longitudinal tabs adapted to fit tightly in said grooves.

5. The assembly of claim 4, wherein said first material is human bone and said second material is surgical implant material.

6. The assembly of claim 5, wherein said surgical implant material is a cotyloid implant part including a shell having a hemispherical outer surface and a truncated pyramidal socket in said shell, and wherein said first fastener and said second fastener protrude from said hemispherical outer surface.

7. An assembly for securing two elements of different hardness, including:

(a) a support made of a first material of a first hardness;

(b) a part made of second material of a second hardness being harder than said first hardness, said part including:

(1) a cylindrical passage in said part and (2) a countersink having internal threads and a first diameter, axially aligned in said part with said passage, including a base; and (c) fastener means for affixing said part and said support and for transferring compressive stress laterally into said part without causing any substantial compression at the interface between the support and the part, said fastener means being anchored in said support and in said part, and said fastener means comprising:

(1) a head having a second diameter less than said first diameter, (2) a rod secured to said support, said rod being axially aligned with and secured to said head, and (3) an externally threaded locking member being threadedly received by said countersink internal threads.

8. An assembly according to claim 2, wherein said fastener means is a screw.

9. An assembly according to claim 8, wherein said countersink internal threads are tapped with a pitch opposite that of threads on said screw.

10. An assembly according to claim 2, wherein said fastener means is a nail.

11. An assembly according to claim 2, wherein said head and said locking member comprise complementary means for lateral holding.

12. The assembly of claim 11, wherein said complementary means for lateral holding comprise a pin protruding from the head of the fastener means and a central hole formed in the locking member.

13. The assembly of claim 8, wherein said head of said screw and the locking member comprise eccentric recesses intended to cooperate with an assembly tool.

14. The assembly of claim 7, wherein the part has a thickness progressively increasing from a zone delimiting a passage.

15. The assembly of claim 7, further including a gusset comprising an external thread and screwed into said part, said gusset delimiting a support surface for the head of the fastener means, a passage for the rod of said fastener means and a countersink provided with an internal thread cooperating with a supplementary locking member.

16. The assembly of claim 15, wherein said gusset comprises, at its periphery, at least one longitudinal groove, and a cap with at least one tab adapted to engage said groove and to lock the gusset in rotation relative to the element in which said gusset is screwed.

17. The assembly according to claim 16, further including a second device arranged obliquely relative to each other.

18. The assembly of claim 7, wherein said support consisting of bone and said part being an implant.

19. The assembly of claim 18, wherein said implant is a cotyloid part including a shell comprising a spherical external surface and an internal surface of truncated pyramid shape, and a jacket of complementary truncated pyramid shape, and wherein fixation devices are arranged in the faces of said shell.

* * * * *